United States Patent
Jani et al.

(10) Patent No.: US 10,443,001 B2
(45) Date of Patent: Oct. 15, 2019

(54) REMOVAL OF SULFUR FROM NAPHTHA

(71) Applicant: UOP LLC, Des Plaines, IL (US)

(72) Inventors: Priyesh Jayendrakumar Jani, Gurgaon (IN); Deepak Bisht, New Delhi (IN); Tuhin Suvra Khan, Gurgaon (IN); Ram Ganesh Rokkam, Visakhapatnam (IN); Pijus Kanti Roy, New Delhi (IN); Steven F. Zink, Westmont, IL (US); Avnish Kumar, Alwar (IN)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/675,025

(22) Filed: Aug. 11, 2017

(65) Prior Publication Data

US 2018/0119032 A1 May 3, 2018

Related U.S. Application Data

(60) Provisional application No. 62/414,594, filed on Oct. 28, 2016.

(51) Int. Cl.
*C10G 45/02* (2006.01)
*B01D 3/14* (2006.01)
(Continued)

(52) U.S. Cl.
CPC ............. *C10G 45/02* (2013.01); *B01D 3/14* (2013.01); *B01D 3/143* (2013.01);
(Continued)

(58) Field of Classification Search
CPC ........ C10G 45/02; C10G 45/44; C10G 35/04; C10G 2400/02; C10G 2300/202;
(Continued)

(56) References Cited

U.S. PATENT DOCUMENTS 2,882,244 A 4/1959 Milton
4,980,046 A 12/1990 Zarchy et al.
(Continued)

FOREIGN PATENT DOCUMENTS

WO 2007008464 A1 1/2007
WO 2013065007 A1 5/2013

OTHER PUBLICATIONS

HP Innovations, "HP innovations: Process removes sulfur, octane not reduced," Hydrocarbon Processing, Feb. 2001, v. 80 n. 2 p. 33.
(Continued)

*Primary Examiner* — Randy Boyer
*Assistant Examiner* — Juan C Valencia
(74) *Attorney, Agent, or Firm* — Paschall & Maas Law Office, LLC; James C. Paschall

(57) ABSTRACT

A process and apparatus for reducing the sulfur content of naphtha. The process includes introducing at least a portion of a naphtha feed stream to a selective hydrodesulfurization zone under selective hydrodesulfurization conditions in the presence of a selective hydrodesulfurization catalyst to form a low sulfur stream which contains mercaptan and thiophene compounds. At least a portion of the low sulfur stream is separated into at least two streams, a mercaptan rich stream containing mercaptan and thiophene compounds and an overhead stream containing hydrogen sulfide and liquid petroleum gas. The mercaptan rich stream is treated in an adsorbent zone to remove at least a portion of the mercaptan and thiophene compounds to form a mercaptan lean stream.

18 Claims, 6 Drawing Sheets

(51) Int. Cl.
- *B01D 53/14* (2006.01)
- *B01D 53/52* (2006.01)
- *C07C 5/02* (2006.01)
- *C10G 35/04* (2006.01)
- *C10G 45/44* (2006.01)
- *C07C 7/148* (2006.01)
- *B01J 23/85* (2006.01)
- *C07C 9/22* (2006.01)
- *C07C 15/20* (2006.01)
- *C07D 335/08* (2006.01)

(52) U.S. Cl.
CPC ......... *B01D 53/1468* (2013.01); *B01D 53/52* (2013.01); *C07C 5/02* (2013.01); *C07C 7/148* (2013.01); *C10G 35/04* (2013.01); *C10G 45/44* (2013.01); *B01J 23/85* (2013.01); *C07C 9/22* (2013.01); *C07C 15/20* (2013.01); *C07D 335/08* (2013.01); *C10G 2300/202* (2013.01); *C10G 2400/02* (2013.01)

(58) Field of Classification Search
CPC ...... B01D 53/1468; B01D 3/14; B01D 53/52; B01J 23/85; C07C 15/20; C07C 5/02; C07C 9/22; C07D 335/08
See application file for complete search history.

(56) References Cited

U.S. PATENT DOCUMENTS

| | | |
|---|---|---|
| 5,730,860 A | 3/1998 | Irvine |
| 5,919,354 A | 7/1999 | Bartek |
| 6,579,444 B2 | 6/2003 | Feimer et al. |
| 7,799,210 B2* | 9/2010 | Dysard ................. C10G 45/08 208/212 |
| 8,057,661 B2 | 11/2011 | Keckler et al. |
| 8,158,843 B2 | 4/2012 | Song et al. |
| 8,366,913 B2 | 2/2013 | Choi et al. |
| 2003/0127362 A1* | 7/2003 | Halbert ............. C10G 67/0418 208/212 |
| 2010/0294698 A1 | 11/2010 | e Mello et al. |
| 2013/0109895 A1 | 5/2013 | Novak et al. |
| 2013/0202511 A1 | 8/2013 | Kanazirev et al. |
| 2014/0110629 A1 | 4/2014 | Flores Sanchez et al. |
| 2015/0122702 A1 | 5/2015 | Choi et al. |

OTHER PUBLICATIONS

Leping, "Process selection for production of ultra-low sulfur gasoline," Petroleum Refinery Engineering, Dec. 2012, v. 42, n. 12, pp. 32-35. Language: Chinese.
Salem, "Removal of sulfur compounds from naphtha solutions using solid adsorbents," Chemical Engineering and Technology, Jun. 1997, v. 20 n. 5, pp. 342-347.
Search Report dated Dec. 28, 2017 for corresponding PCT Appl. No. PCT/US2016/052625.

* cited by examiner

REMOVAL OF SULFUR FROM NAPHTHA

CROSS-REFERENCE TO RELATED APPLICATION

This application claims priority from Provisional Application No. 62/414,594 filed Oct. 28, 2016, the contents of which cited application are hereby incorporated by reference in its entirety.

BACKGROUND OF THE INVENTION

The Euro V standard for the level of sulfur in gasoline is 10 wt ppm sulfur. Special processing is need to obtain these sulfur levels.

Gasoline from fluid catalytic cracking (FCC) processes comprises up to 50 vol % of a refinery's motor gasoline pool, and up to 90% of the motor gasoline pool's sulfur content. Consequently, it is important that the treatment of this stream not significantly reduce its octane contribution to the pool.

In order to obtain the needed sulfur levels, the majority of gasoline worldwide obtained from fluid catalytic cracking (FCC) processes is selectively hydrodesulfurized which generally preserves the alkenes and aromatics. Typical processing conditions for hydrodesulfurization include a temperature of about 250° C. to about 315° C. and a pressure of about 1.7 MPa(g) to about 17-26 bar(g) with a supported CoMo catalyst.

However, selective hydrodesulfurization cannot bring down the sulfur level down sufficiently to meet the 10 wt ppm due to formation of recombinant mercaptans. The $H_2S$ produced during the selective hydrodesulfurization reaction stage reacts with olefins present in the effluent to form mercaptans, predominantly butyl mercaptans. In addition, the current selective hydrodesulfurization catalytic system and the operating conditions are not optimized to target the reduction of the recombinant mercaptans in the selective hydrodesulfurization reaction stage.

Consequently, in order meet this limit, some refiners have added a polishing reactor downstream of the selective hydrodesulfurization reactor. Typically, the polishing reactor uses a Ni based catalyst with LHSV of about 1 $hr^{-1}$ and a temperature of about 280° C. to about 380° C. The polishing reactor reduces the mercaptans especially by saturating the olefins and thereby reducing the equilibrium mercaptans in the reactor effluent. However, saturating the olefins reduces the octane content.

Therefore, there is a need for improved processes for desulfurizing gasoline.

SUMMARY OF THE INVENTION

One aspect of the invention is a process for reducing the sulfur content of naphtha. In one embodiment, the process includes introducing at least a portion of a naphtha feed stream to a selective hydrodesulfurization zone under selective hydrodesulfurization conditions in the presence of a selective hydrodesulfurization catalyst to form a low sulfur stream, which contains mercaptan compounds and thiophene compounds. At least a portion of the low sulfur stream is separated into at least two streams, a mercaptan rich stream containing mercaptan compounds and thiophene compounds and an overhead stream containing hydrogen sulfide and liquid petroleum gas. The mercaptan rich stream is treated in an adsorbent zone to remove at least a portion of the mercaptan compounds and the thiophene compounds to form a mercaptan lean stream.

Another aspect of the invention is an apparatus for reducing the sulfur content of naphtha. In one embodiment, the apparatus includes a selective hydrodesulfurization zone having an inlet and an outlet; a stripper column having an inlet, an overhead vapor outlet, and a liquid outlet, the outlet of the selective hydrodesulfurization zone being in fluid communication with the inlet of the stripper column; and an adsorbent zone having an inlet and an outlet, the liquid outlet of the stripper column being in fluid communication with the inlet of the adsorbent zone.

DETAILED DESCRIPTION OF THE INVENTION

Figure 1:
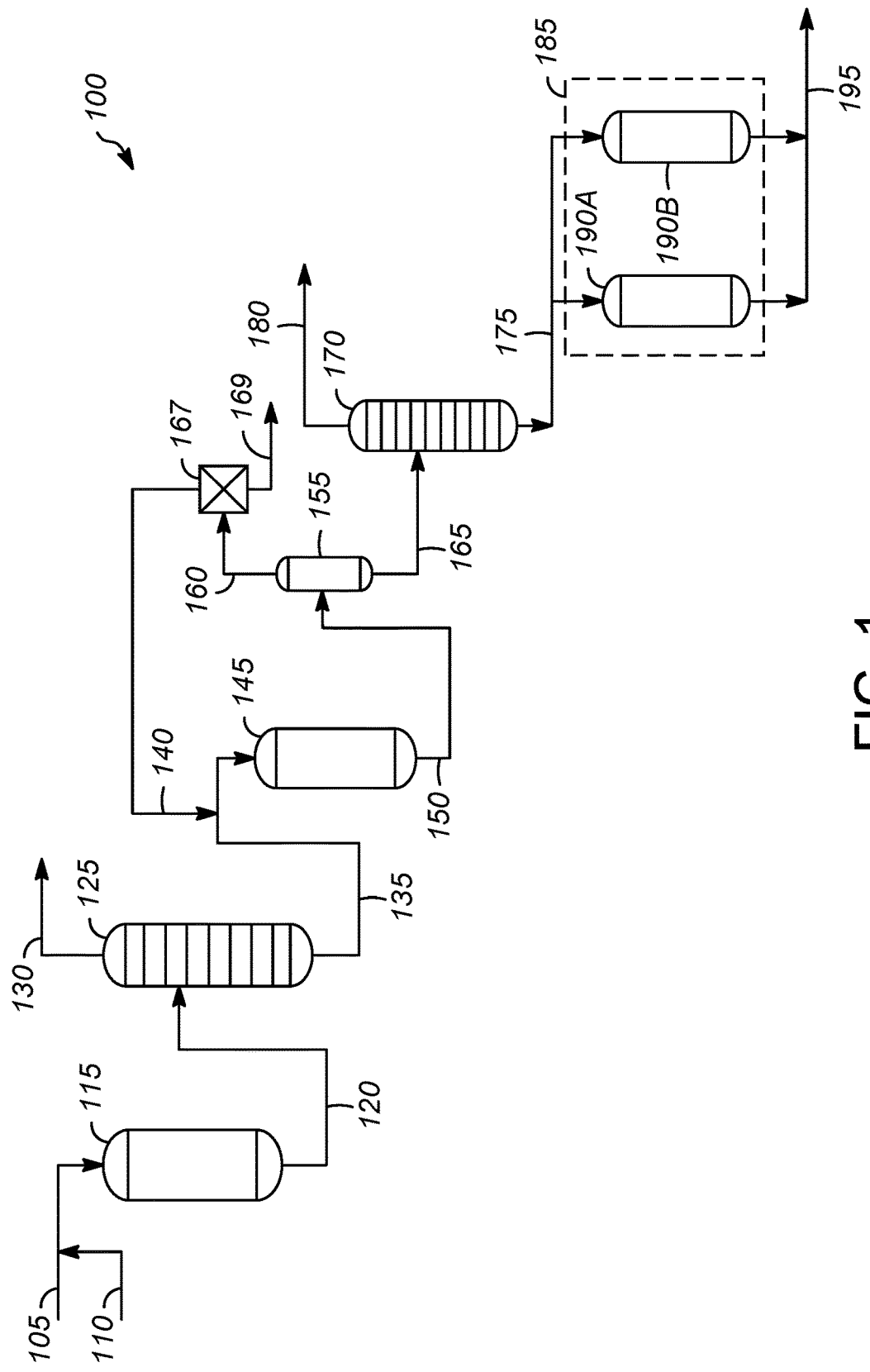
FIG. 1 is an illustration of one embodiment of the process of the present invention.

Several approaches have been developed to manage the sulfur left in naphtha after the selective hydrodesulfurization reaction zone, which can include mercaptan compounds and thiophene compounds. All of the processes involve treating at least a portion of the effluent from the selective hydrodesulfurization zone in an adsorbent zone to remove the mercaptan and thiophene compounds.

The naphtha feed typically has a sulfur content of about 100-5000 wt ppm sulfur, a diolefin content of about 500-4000 wt ppm, and an olefin content of about 15-50 wt %. In some embodiments, the naphtha feed is a full range FCC naphtha feed.

Some embodiments begin with the treatment of the naphtha feed in a selective hydrogenation zone to hydrogenate the diolefins in the feed, which reduces the diolefin content to about 10-100 wt ppm.

The hydrogenated feed is optionally separated in a splitter column into at least two fractions, a light fraction and a heavy fraction. The light fraction will typically have less than 10 wt ppm sulfur and can be sent to the gasoline pool for blending.

The heavy fraction, which typically contains more than about 100-5000 wt ppm sulfur, is sent to the selective hydrodesulfurization zone where the sulfur in the feed is converted to hydrogen sulfide, and some of the hydrogen sulfide further reacts with olefins in the feed to form mercaptides and thiophenes.

The effluent from the selective hydrodesulfurization zone, which contains about 20-100 wt ppm sulfur, is sent to a stripper column and separated into at least an overhead vapor stream, and a mercaptan rich stream. The overhead stream contains hydrogen sulfide and liquid petroleum gas (LPG). The mercaptan rich stream contains the mercaptan and thiophene compounds. The mercaptan rich stream is treated in the adsorption zone to remove the mercaptan and thiophene compounds to form a mercaptan lean stream. The mercaptan lean stream has less mercaptan and thiophene compounds than the mercaptan rich stream introduced into the adsorption zone, e.g., than 10 wt ppm sulfur. The mercaptan lean stream can be blended with the gasoline pool.

In some embodiments, the only streams formed in the stripper column are the overhead stream and the mercaptan rich stream.

In other embodiments, the effluent from the selective hydrodesulfurization zone is separated into at least the overhead vapor stream, the mercaptan rich stream, and a mercaptan lean stream. The mercaptan rich stream is treated in the adsorption zone. The mercaptan lean stream has a low enough level of mercaptan and thiophene compounds that it can be blended with the gasoline pool without further treatment. The mercaptan lean stream can either be a side cut from the splitter or the bottoms stream depending on the specific fractionation being utilized.

In other embodiments, the effluent from the selective hydrodesulfurization zone is separated into at least the overhead vapor stream, the mercaptan rich stream, and a thiophene rich stream. In this case, the mercaptan rich stream is treated in one adsorption zone with a less reactive adsorbent, and the thiophene rich stream is treated in a second adsorption zone with a more reactive adsorbent.

The adsorption zone contains at least one adsorbent bed. There are typically at least two adsorbent beds. In some embodiments, they can be run in a lead/lag mode in which the mercaptan rich stream flows to one bed until that bed is spent, and then the mercaptan rich stream is switched to another bed. The first bed is then regenerated or replaced.

The adsorbent can be regenerative or non-regenerative or mixtures of the two.

Suitable adsorbents include, but are not limited to, molecular sieves, metal loaded alumina, an alumina-zeolite composite, reactive metal adsorbents, or combinations thereof. The metal loaded alumina adsorbent contains at least one metal from Groups IB, IIB, VIIB, and VIIIB of the periodic table. The reactive metal adsorbents are metal or metal oxides in a reduced oxidation state. The metals include, but are not limited to, Cu, Fe, Zn, Mn, and the like. When reactive metals are used as the adsorbent, the adsorption zone is typically operated in the substantial absence of hydrogen so the adsorbent does not react with the olefins in the stream. Examples of adsorbents include clay based Type X molecular sieves, and Cu or Cu-oxide on alumina or clay.

In other embodiments, a caustic extraction zone precedes the selective hydrodesulfurization zone, rather than the selective hydrogenation zone.

FIG. 1 illustrates one embodiment of the process 100. The naphtha feed 105 is mixed with hydrogen 110 and introduced into the selective hydrogenation zone 115. The selective hydrogenation zone 115 is normally operated at relatively mild hydrogenation conditions. These conditions will normally result in the hydrocarbons being present as liquid phase materials. The reactants will normally be maintained under the minimum pressure sufficient to maintain the reactants as liquid phase hydrocarbons. A broad range of suitable operating pressures therefore extends from about 276 kPa(g) to about 5516 kPa(g) (about 40 psig to about 800 psig), or about 1379 kPa(g) to about 3102 kPa(g) (about 200 and 450 psig). A relatively moderate temperature between about 25° C. and about 350° C. (about 77° F. to about 662° F.), or about 50° C. and about 200° C. (about 122° F. to about 392° F.)), or about 130° C. and about 200° C. (about 266° F. to about 392° F.) is typically employed. The liquid hourly space velocity of the reactants through the selective hydrogenation catalyst should be above about 1.0 hr$^{-1}$, or above about 3.0 hr$^{-1}$, or between about 3.0 hr$^{-1}$ and about 35.0 hr$^{-1}$. Another variable operating condition is the ratio of hydrogen to diolefinic hydrocarbons maintained within the selective hydrogenation zone 115. The amount of hydrogen required to achieve a certain conversion is believed dependent upon both reactor temperature and the molecular weight of the feed hydrocarbons. To avoid the undesired saturation of a significant amount monoolefinic hydrocarbons, there should be less than 2.0 times the stoichiometric amount of hydrogen required for the selective hydrogenation of the diolefinic hydrocarbons which are present in the liquid phase process stream to monoolefinic hydrocarbons. Preferably, the mole ratio of hydrogen to diolefinic hydrocarbons in the material entering the bed of selective hydrogenation catalyst is maintained between 1:1 and 1.8:1. In some instances, it may be desirable to operate with a less than stoichiometrically required amount of hydrogen, with mole ratios down to 0.75:1 being acceptable. The optimum set of conditions will of course vary depending on such factors as the composition of the feed stream and the degree of saturation of diolefinic hydrocarbons which it is desired to perform.

Any suitable catalyst which is capable of selectively hydrogenating diolefins in a naphtha stream may be used. Suitable catalysts include, but are not limited to, at least one Group VIII metal (preferably iron, cobalt and nickel, more preferably cobalt and/or nickel) and at least one Group VI metal (preferably molybdenum and tungsten) on a high surface area support material, preferably alumina. Other suitable hydrotreating catalysts include zeolitic catalysts. Examples of catalysts include titanium, vanadium, chromium, manganese, cobalt, nickel, zinc, molybdenum, and cadmium or mixtures thereof. The metals are preferably supported on inorganic oxide supports such as silica and alumina, for example.

In some embodiments, the catalyst is employed in a fixed bed reactor containing a cylindrical bed of catalyst through which the reactants move in a vertical direction. In some embodiments, the reactants flow upward through the reactor while other embodiments use a downflow arrangement. The subject catalyst may be present within the reactor as pellets, spheres, extrudates, irregular shaped granules, etc. To employ the subject catalyst, the reactants would be preferably brought up to the desired inlet temperature of the reaction zone, admixed with hydrogen and then passed into and through the reactor. Alternatively, the reactants may be admixed with the desired amount of hydrogen and then heated to the desired inlet temperature. In either case, the effluent of the reaction zone may be passed into a product recovery facility for the removal of residual hydrogen or may be passed directly into downstream product utilization zones if the presence of the residual hydrogen is acceptable. Hydrogen may be removed by flashing the effluent stream to a lower pressure or by passing the effluent stream into a stripping column.

The hydrogenated effluent 120 is sent to a splitter column 125 where it is separated into a light fraction 130 and a heavy fraction 135. The light fraction 130 typically has a T5 boiling point of about 0° C. to about 10° C., a T95 boiling point of about 55° C. to about 65° C., and a final boiling point of about 65° C. to about 70° C., and the heavy fraction typically has a T5 boiling point of about 60° C. to about 70° C., a T95 boiling point of about 210° C. to about 240° C., and a final boiling point of about 250° C. to about 280° C.

The heavy fraction 135 is combined with a hydrogen-rich stream 140 and introduced into a selective hydrodesulfurization zone 145 to selectively remove sulfur. The selective hydrodesulfurization zone 145 contains a hydrotreating catalyst (or a combination of hydrotreating catalysts) and operated at selected hydrotreating conditions effective to convert a majority of the sulfur in the feed to hydrogen sulfide and minimize saturation of olefins at the same time. In general, such selective conditions include a temperature from about 250° C. (482° F.) to about 315° C. (600° F.), about 260° C. (500° F.) to about 300° C. (572° F.), a pressure from about 0.69 MPa (100 psig) to about 3.45 MPa (500 psig), a liquid hourly space velocity of the fresh hydrocarbonaceous feedstock from about 0.5 hr$^{-1}$ to about 10 hr$^{-1}$. Other hydrotreating conditions are also possible depending on the particular feed stocks being treated. The selective hydrodesulfurization zone 145 may contain a single or multiple reactor and each reactor may contain one or more reaction zones with the same or different catalysts to convert sulfur and nitrogen to hydrogen sulfide and ammonia.

Suitable hydrodesulfurization catalysts are any known conventional hydrotreating catalysts and include those which are comprised of at least one Group VIII metal (preferably iron, cobalt and nickel, more preferably cobalt and/or nickel) and at least one Group VI metal (preferably molybdenum and tungsten) on a high surface area support material, preferably alumina. Other suitable hydrotreating catalysts include zeolitic catalysts. It is within the scope of the processes herein that more than one type of hydrotreating catalyst be used in the same reaction vessel. The Group VIII metal is typically present in an amount ranging from about 0.5 to about 20 weight percent, preferably from about 0.5 to about 10 weight percent. The Group VI metal will typically be present in an amount ranging from about 1 to about 25 weight percent, and preferably from about 1 to about 12 weight percent. While the above describes some exemplary catalysts for hydrotreating, other hydrotreating and/or hydrodesulfurization catalysts may also be used depending on the particular feedstock and the desired effluent quality.

The conditions in the selective hydrodesulfurization zone 145 are effective to convert greater than about 50 percent of the sulfur in the heavy fraction 135 to hydrogen sulfide and, preferably, about 60 to about 80 percent of the sulfur to hydrogen sulfide. At the same time, the selected conditions disfavor olefin saturation to generally maintain the octane level. However, at these conditions, some of the hydrogen sulfide produced reacts to form mercaptans. These reactions are often called reversion or recombination reactions.

The effluent 150 from the selective hydrodesulfurization zone 145 can have a T5 boiling point of about 65° C. to about 70° C., a T95 boiling point of about 210° C. to about 240° C., and a final boiling point of about 250° C. to about 280° C.

The effluent 150 from the selective hydrodesulfurization zone 145 is sent to a separator 155 where it is separated into a hydrogen rich stream 160 and a liquid stream 165. The hydrogen rich stream 160 is sent to a hydrogen sulfide scrubber 167 to remove hydrogen sulfide 169 and form hydrogen rich stream 140.

Liquid stream 165 from the separator 155 is sent to a stripper zone 170 where it is separated into at least two streams. As illustrated in FIG. 1, liquid stream 165 is separated into a mercaptan rich stream 175 and an overhead stream 180. The overhead stream 180 contains hydrogen sulfide and LPG and can be sent for further processing (not shown).

In this embodiment, the mercaptan rich stream 175 has a T5 boiling point of about 20° C. to about 40° C., a T95 boiling point of about 210° C. to about 240° C., and a final boiling point of about 250° C. to about 280° C.

The mercaptan rich stream 175 is sent to an adsorption zone 185. The adsorption zone 185 contains one or more adsorbent beds 190A, 190B containing an adsorbent. As illustrated, the adsorbent beds 190A, 190B are operated in a swing bed arrangement in which the mercaptan rich stream is sent to adsorbent bed 190A, and when adsorbent bed 190A is spent, the mercaptan rich stream 175 is sent to adsorbent bed 190B.

The adsorbent can be regenerative or non-regenerative. If a regenerative adsorbent is used, adsorbent bed 190A is regenerated while adsorbent bed 190B is being used. If a non-regenerative adsorbent is used, the adsorbent is replaced.

Suitable adsorbents include, but are not limited to, molecular sieves, metal loaded alumina, alumina-zeolite composite adsorbents, reactive metal adsorbents, or combinations thereof. Suitable molecular sieves include, but are not limited to type X molecular sieves. Type X molecular sieve belongs to the faujasite family of zeolites. Its synthesis was first reported in U.S. Pat. No. 2,882,244 which is incorporated by reference. Zeolite X has the empirical formula:

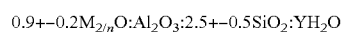

$$0.9+-0.2M_{2/n}O:Al_2O_3:2.5+-0.5SiO_2:YH_2O$$

where M is an alkali or alkaline earth metal, "n" is the valence of M and "Y" has a value up to 8. Briefly, zeolite X is prepared by forming a reaction mixture containing reactive sources of the components, reacting the mixture at a temperature of about 21° C. to about 120° C. for a time of about 1 hours to about 100 hours. Zeolite X is usually synthesized in the sodium form. That is, sodium is the counter ion present in the pores of the zeolite.

Metal loaded adsorbents can be prepared by well known extrusion or co-nodulization (agglomeration) methods as described in application US 2013/0202511 A1. The metal loaded adsorbent contains at least one metal from Groups IB, IIB, VIIB, and VIIIB of the periodic table. In some embodiments, it can be metal loaded alumina having a surface area of at least 150 m$^2$/g, and mixtures thereof.

The reactive metal adsorbents are metal or metal oxides in a reduced oxidation state. The metals include, but are not limited to, Cu, Fe, Zn, Mn, and the like. When reactive metals are used as the adsorbent, the adsorption zone is operated in the substantial absence of hydrogen so the adsorbent does not react with the olefins in the stream.

Contacting of the liquid hydrocarbon stream with any of the adsorbents described above can be carried out by means well known in the art. For example, the contacting can be carried out in a batch mode or in a continuous mode. In a batch mode, the stream to be treated is mixed with a sufficient amount of adsorbent in an appropriate size reaction vessel. The resultant mixture can be stirred or agitated to ensure complete contact of the stream with the adsorbent. In order to ensure that the sulfur compounds are completely adsorbed onto the support, it is necessary that the hydrocarbon stream be contacted with the solid solution for a time of about 10 minutes to about 10 hours. If a continuous process is used, the adsorbent is placed in a vertical column and the stream to be treated is upflowed through the column. The stream is flowed at a liquid hourly space velocity of about 0.1 hr$^{-1}$ to about 10 hr$^{-1}$.

Whether the process is carried out in a batch or continuous manner, the adsorbent can be used in the form of extrudates, pills, beads, spheres, etc. Usually, the adsorbent is mixed with a binder such as attapulgite clay, minugel clay and bentonite clay and then formed into the desired shape. The amount of binder which is used varies from about 8 to about 20 wt. %. Processes for forming the various shapes are well known in the art.

Finally, the contacting can be carried out over a broad temperature range. Generally the temperature range is from about 10° C. to about 200° C., or about 20° C. to about 200° C., or about 20° C. to about 100° C., or about 20° C. to about 70° C. The process is conducted at atmospheric pressure or pressures up to about 1379 kPa (g) (about 200 psig).

Following treatment in the adsorption zone 185, the mercaptan lean stream 195, which has less than 10 wt ppm sulfur, can be sent to the gasoline pool for blending.

Figure 2:
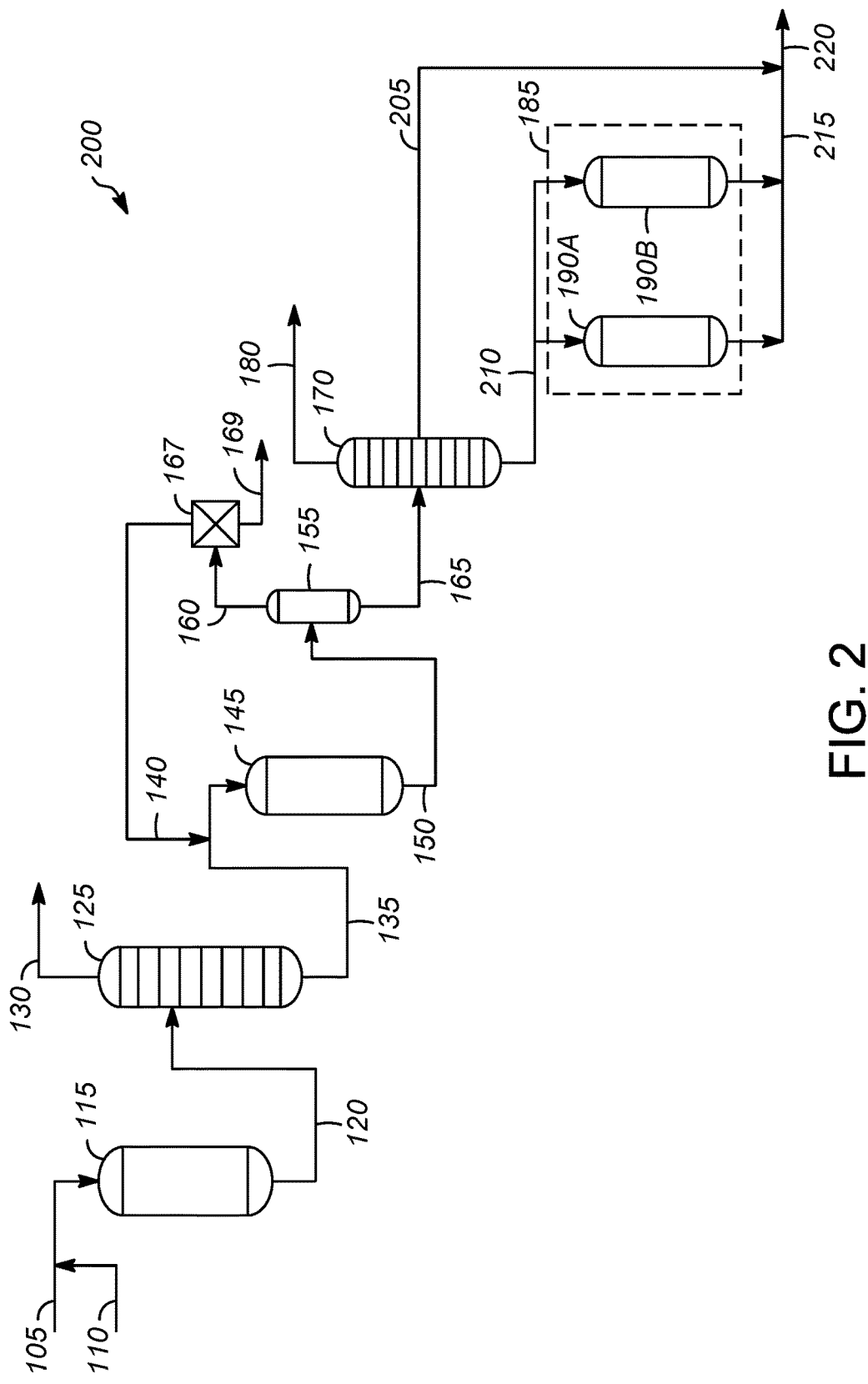
FIG. 2 is an illustration of another embodiment of the process of the present invention.

FIG. 2 illustrates another embodiment of the process 200. The naphtha feed 105 is sent to the selective hydrogenation zone 115. The hydrogenated effluent 120 is separated in splitter column 125, and the heavy fraction 135 is sent to the selective hydrodesulfurization zone 145. The effluent 150 from the selective hydrodesulfurization zone 145 is sent to the separator 155.

The liquid stream 165 from the separator 155 is sent to the stripper zone 170 where it is separated into overhead stream 180, a mercaptan lean stream 205, and mercaptan rich stream 210. The mercaptan lean stream 205 has a T5 boiling point of about 20° C. to about 40° C., a T95 boiling point of about 55° C. to about 65° C., and a final boiling point of greater than about 70° C. to about 75° C. The mercaptan rich stream 210 has a T5 boiling point of about 60° C. to about 70° C., a T95 boiling point of about 210° C. to about 240° C., and a final boiling point of about 250° C. to about 280° C.

The mercaptan rich stream 210 is treated in the adsorption zone 185.

Following treatment in the adsorption zone 185, the mercaptan lean stream 215 has less than 10 wt ppm sulfur. It can be combined with the mercaptan lean stream 205 to form mercaptan lean stream 220 which can be sent to the gasoline pool for blending.

Figure 3:
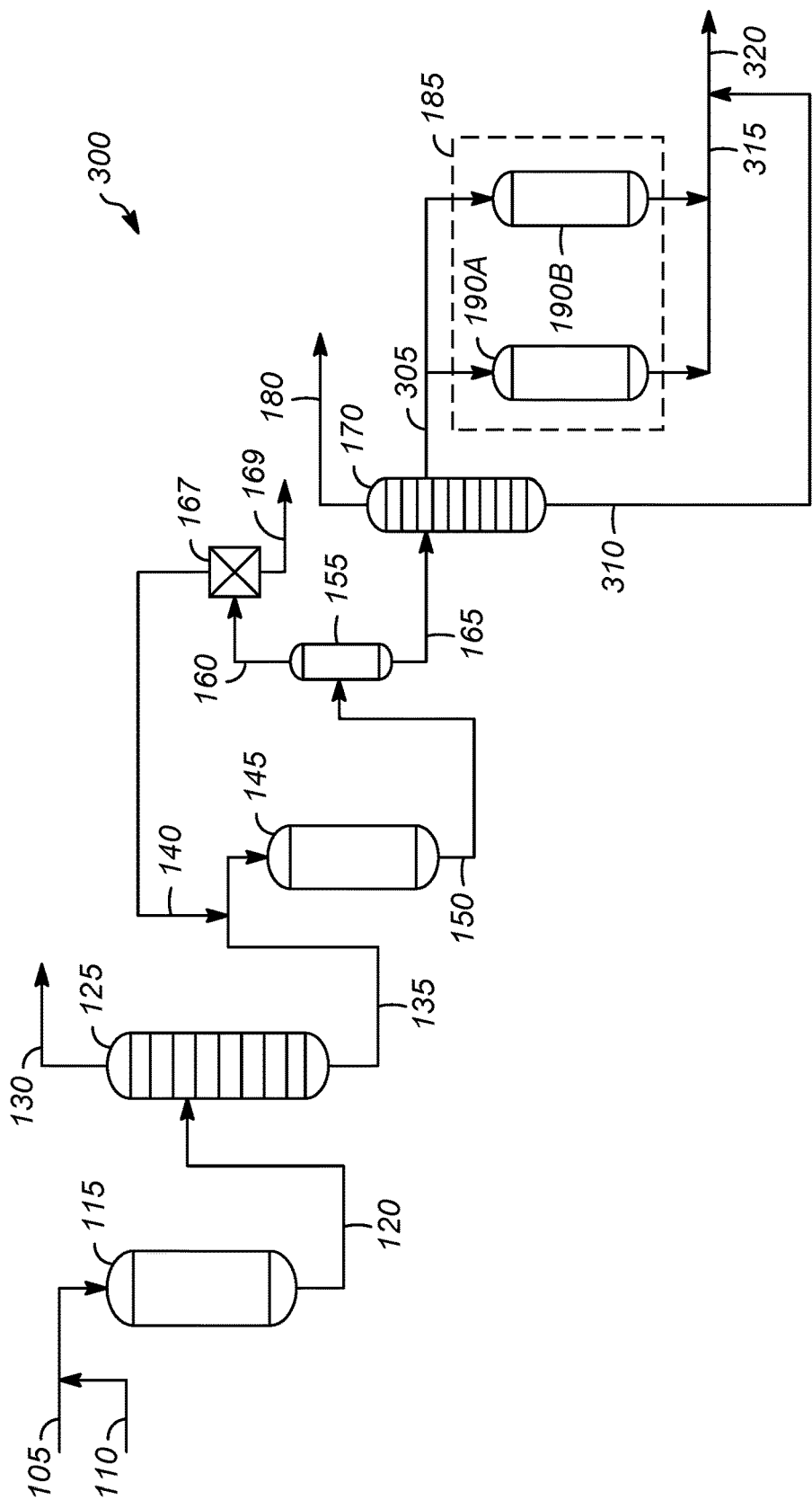
FIG. 3 is an illustration of still another embodiment of the process of the present invention.

FIG. 3 illustrates another embodiment of the process 300. The naphtha feed 105 is sent to the selective hydrogenation zone 115. The hydrogenated effluent 120 is separated in splitter column 125, and the heavy fraction 135 is sent to the selective hydrodesulfurization zone 145. The effluent 150 from the selective hydrodesulfurization zone 145 is sent to the separator 155.

The liquid stream 165 from the separator 155 is sent to the stripper zone 170 where it is separated into overhead stream 180, a mercaptan rich stream 305 which may be taken from a side of the stripper zone 170, and mercaptan lean stream 310 which may be taken from a bottom of the stripper zone 170. The mercaptan rich stream 305 has a T5 boiling point of about 20° C. to about 40° C., a T95 boiling point of about 95° C. to about 105° C., and a final boiling point of about 110° C. to about 130° C.

The mercaptan lean stream 310 has a T5 boiling point of about 100° C. to about 110° C., a T95 boiling point of about 210° C. to about 240° C., and a final boiling point of about 250° C. to about 280° C.

After treatment in the adsorption zone 185, the mercaptan lean stream 315 has less than 10 wt ppm sulfur. It can be combined with the mercaptan lean stream 310 to form mercaptan lean stream 320, which can be sent to the gasoline pool for blending.

Figure 4:
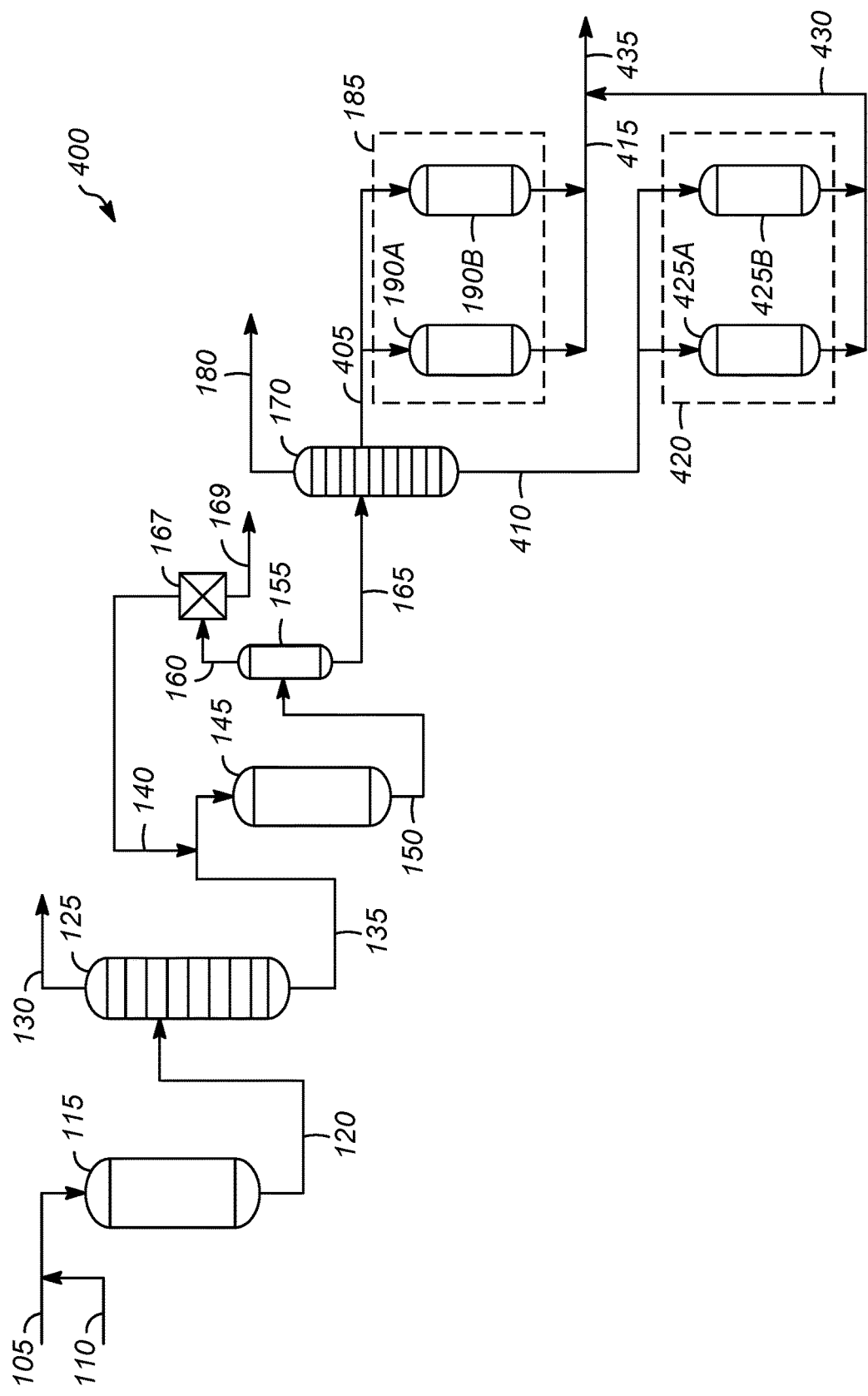
FIG. 4 is an illustration of yet another embodiment of the process of the present invention.

FIG. 4 illustrates another embodiment of the process 400. The naphtha feed 105 is sent to the selective hydrogenation zone 115. The hydrogenated effluent 120 is separated in splitter column 125, and the heavy fraction 135 is sent to the selective hydrodesulfurization zone 145. The effluent 150 from the selective hydrodesulfurization zone 145 is sent to the separator 155.

The liquid stream 165 from the separator 155 is sent to the stripper zone 170 where it is separated into overhead stream 180, a mercaptan rich stream 405 which may be taken from a side of the stripper zone 170, and thiophene rich stream 410 which may be taken from a bottom of the stripper zone 170. The mercaptan rich stream 405 has a T5 boiling point of about 20° C. to about 40° C., a T95 boiling point of about 95° C. to about 105° C., and a final boiling point of about 110° C. to about 130° C.

The thiophene rich stream 410 has a T5 boiling point of about 100° C. to about 110° C., a T95 boiling point of about 210° C. to about 240° C., and a final boiling point of about –250° C. to about 280° C.

The adsorption zone 185 contains a less reactive adsorbent. Because the mercaptan rich stream 405 contains some amount of olefin, the surface acidity of the adsorbent should be reduced to avoid olefin oligomerization, which could lead to coke formation during regeneration at high temperature. Therefore, the surface acidity of the adsorbent is reduced by known methods, including but not limited to, alkali metal doping, yielding a less reactive adsorbent. The sulfur compounds removed in the adsorption zone 185 are removed by physical adsorption and thus the adsorbent is regenerable. After treatment in the adsorption zone 185, the mercaptan lean stream 415 has less than 10 wt ppm sulfur.

The thiophene rich stream 410 is treated in a second adsorption zone 420 which contains adsorbent beds 425A and 425B. The adsorbent beds 425A and 425B contain a more reactive adsorbent. In general, thiophene compounds cannot be removed by regenerative molecular sieve based adsorbents. Therefore, a metal loaded reactive adsorbent is typically used. A chemical reaction occurs to remove sulfur compounds. Consequently, the adsorbent is not regenerable.

Following treatment in the adsorption zone 420, the thiophene lean stream 430 has less than about 10 wt ppm sulfur.

The thiophene lean stream 430 can be combined with the mercaptan lean stream 415 to form mercaptan and thiophene lean stream 435, which can be sent to the gasoline pool for blending.

Figure 5:
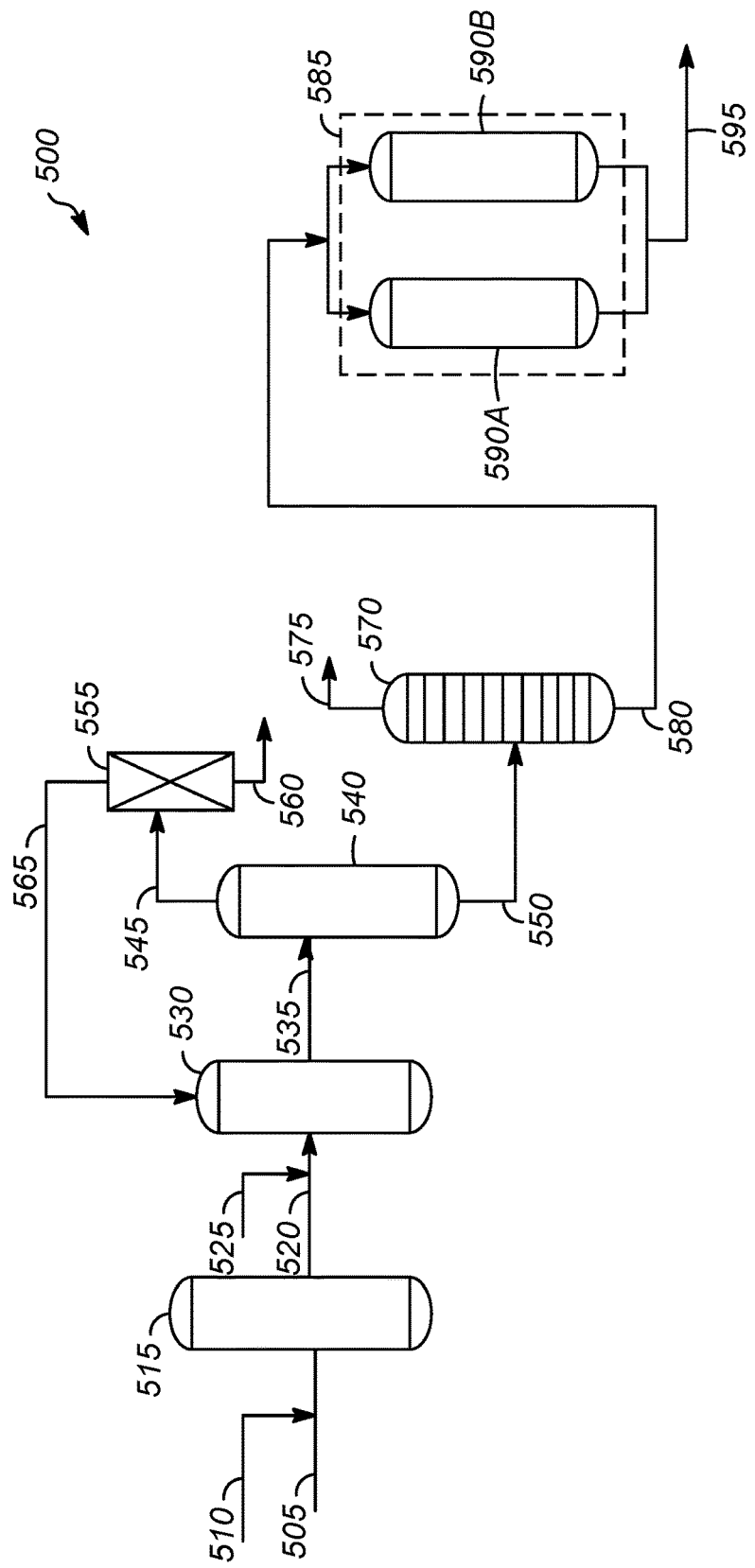
FIG. 5 is an illustration of another embodiment of the process of the present invention.

FIG. 5 illustrates another embodiment of the process 500. In this embodiment, there is no splitter column.

The naphtha feed 505 is mixed with hydrogen 510 and sent to the selective hydrogenation zone 515. The hydrogenated effluent 520 is mixed with hydrogen 525 and sent to the selective hydrodesulfurization zone 530.

The effluent 535 from the selective hydrodesulfurization zone 530 is sent to the separator 540 where it is separated into a hydrogen rich stream 545 and a liquid stream 550. The hydrogen rich stream 545 is sent to a hydrogen sulfide scrubber 555 to remove hydrogen sulfide 560 and form hydrogen rich stream 565.

The liquid stream 550 from the separator 540 is sent to the stripper zone 570 where it is separated into overhead stream 575 and a mercaptan rich stream 580. The mercaptan rich stream 580 has a T5 boiling point of about 30° C. to about 40° C., a T95 boiling point of about 220° C. to about 240° C., and a final boiling point of about 250° C. to about 280° C.

The mercaptan rich stream 580 is treated in the adsorption zone 585 which includes adsorbent beds 590A and 590B.

Following treatment in the adsorption zone 585, the mercaptan lean stream 595 has less than 10 wt ppm sulfur. It can be sent to the gasoline pool for blending.

The alternate embodiments for the separation in the stripper zone illustrated in FIGS. 2-4 could be used here as well.

Figure 6:
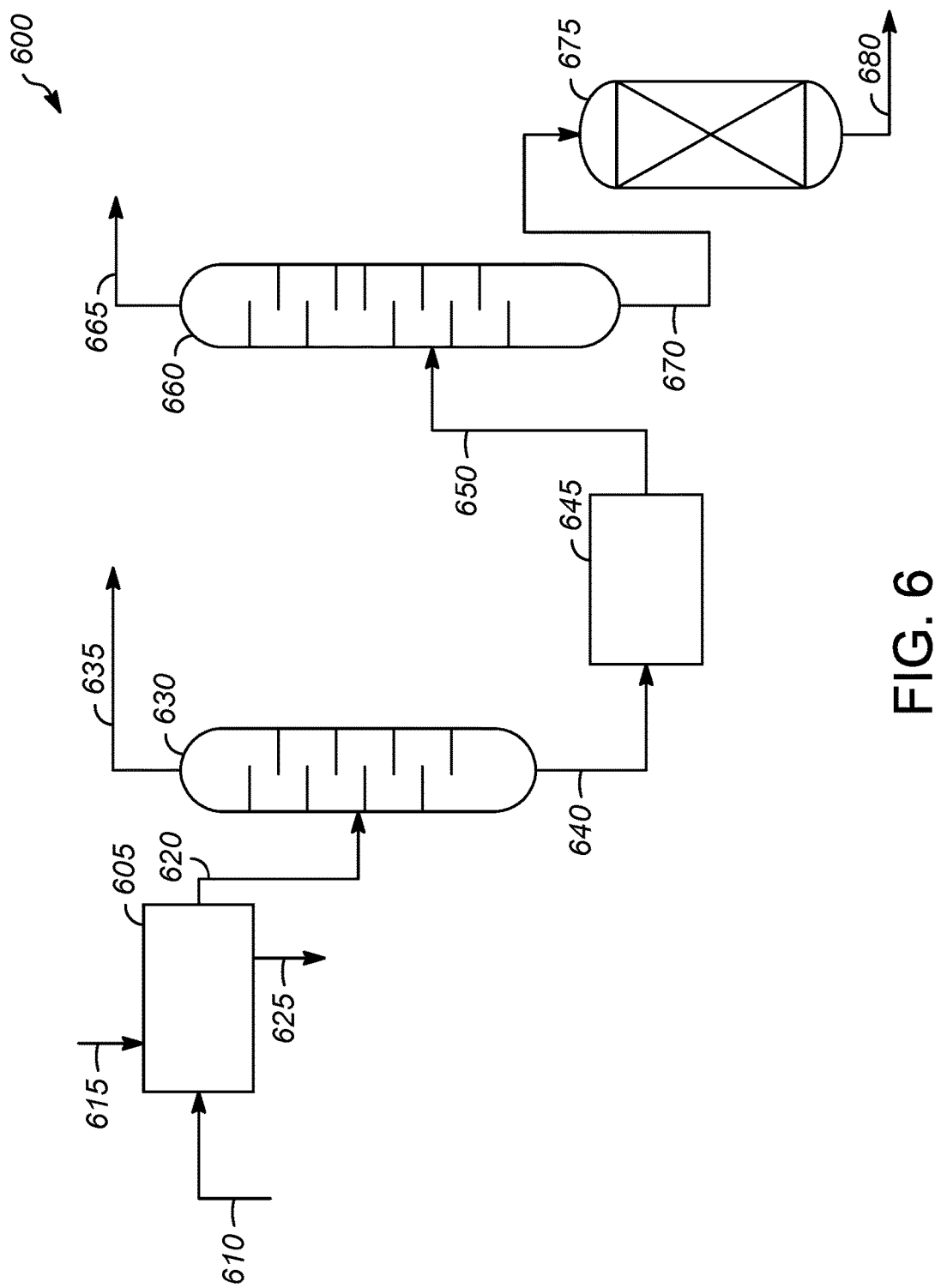
FIG. 6 is an illustration of another embodiment of the process of the present invention.

FIG. 6 illustrates another embodiment of the process 600 which utilizes a caustic extraction zone 605.

The naphtha stream 610 is fed to the caustic extraction zone 605 along with a sulfur lean caustic stream 615. The sulfur lean caustic stream 615 contacts the naphtha stream 610. The caustic extraction process may utilize any alkaline reagent which is capable of extracting sulfur from the feed stream at practical operating conditions and which may be regenerated in the manner described. A preferred alkaline reagent comprises an aqueous solution of an alkaline metal hydroxide, such as sodium hydroxide or potassium hydroxide. Sodium hydroxide, commonly referred to as caustic, may be used in concentrations of from 1 to 50 wt. %, with a preferred concentration range being from about 5 to about 25 wt. %. Optionally, there may be added an agent to increase the solubility of the mercaptans in the solution, typically methanol or ethanol although others such as a phenol, cresol or butyric acid may be used.

The conditions employed in the caustic extraction zone 605 may vary greatly depending on such factors as the nature of the hydrocarbon stream being treated and its sulfur content, etc. In general, the extraction may be performed at an ambient temperature above about 15.6° C. (about 60° F.) and at a pressure sufficient to ensure liquid state operation. The pressure may range from atmospheric up to about 6.9 MPa (g) (about 1000 psig) or more, but a pressure in the range of from about 345 kPa(g) to about 1034 kPa(g) (about 50 psig to about 150 psig) is preferred.

A second consideration is that the pressure chosen should ensure an adequate amount of oxygen is dissolved in the alkaline stream in the downstream oxidation step (not shown), which if practical is preferably operated at substantially the same pressure as the caustic extraction zone after normal process flow pressure drops are taken into consideration. The temperature in the caustic extraction zone 605 is desirably in the range of about 10° C. to about 121° C. (about 50° F. to about 250° F.), or about 26.7° C. to about 48.9° C. (about 80° F. to about 120° F.). The ratio of the volume of the alkaline solution required per volume of the feed stream will vary depending on the mercaptan content of the feed stream. Normally this ratio will be between 0.01:1 and 1:1, although other ratios may be desirable. The rate of flow of the alkaline solution will typically be in the range of about 5 wt ppm to about 30 wt ppm of the flow of the mercaptan rich stream 185. Optimum extraction in this liquid system is obtained with a velocity through the perforations of from about 5 to about 10 feet per second. Essentially all of the extractable mercaptans should be transferred to the alkaline solution from the feed stream. As used herein, the term "essentially all" is intended to refer to at least 95% and preferably 98% of all the material referred to.

The sulfur is transferred from the naphtha stream 610 to the sulfur lean caustic stream 615, resulting in a reduced sulfur stream 620 and a sulfur rich caustic stream 625.

The sulfur rich caustic stream 625 can be sent for treatment to remove the sulfur (not shown) and recycled to the caustic extraction zone 605, if desired.

The reduced sulfur stream 620 is separated in splitter column 630 into a light fraction 635 and a heavy fraction 640.

The light fraction has a T5 boiling point of about 0° C. to about 10° C., a T95 boiling point of about 55° C. to about 65° C., and a final boiling point of about 65° C. to about 70° C., and heavy fraction having a T5 boiling point of about 60° C. to about 70° C., a T95 boiling point of about 210° C. to about 240° C., and a final boiling point of about 250° C. to about 280° C.

The heavy fraction 640 is sent to the selective hydrodesulfurization zone 645. The effluent 650 from the selective hydrodesulfurization zone 645 is sent to the stripper zone 660 where it is separated into overhead stream 665 and a mercaptan rich stream 670. The mercaptan rich stream 670 has a T5 boiling point of about 30° C. to about 40° C., a T95 boiling point of about 220° C. to about 240° C., and a final boiling point of about 250° C. to about 280° C.

The mercaptan rich stream 670 is sent to the adsorption zone 675. In this embodiment, there is only one adsorbent bed in the adsorption zone. In other embodiments, there could be two or more adsorbent beds as described above.

The mercaptan light stream 680 from adsorption zone 675, which has less than 10 wt ppm sulfur, can be sent to the gasoline pool for blending.

The alternate embodiments for the separation in the stripper zone illustrated in FIGS. 2-4 could be used here as well.

By the term "about," we mean that within 10% of the specified value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for reducing the sulfur content of full range naphtha comprising introducing at least a portion of a naphtha feed stream to a selective hydrodesulfurization zone under selective hydrodesulfurization conditions in the presence of a selective hydrodesulfurization catalyst to form a low sulfur stream, the low sulfur stream containing mercaptan compounds and thiophene compounds; separating at least a portion of the low sulfur stream into at least two streams, a mercaptan rich stream containing mercaptan compounds and thiophene compounds and an overhead stream containing hydrogen sulfide and liquid petroleum gas; and treating the mercaptan rich stream in an adsorbent zone to remove at least a portion of the mercaptan compounds and the thiophene compounds to form a mercaptan lean stream. An embodiment of the invention is one, any or all of prior embodiments in this paragraph up through the first embodiment in this paragraph wherein separating the at least the portion of the low sulfur stream into at least two streams comprises separating the at least the portion of the low sulfur stream into the mercaptan rich stream, the overhead stream, and a second mercaptan lean stream. An embodiment of the invention is one, any or all of prior embodiments in this paragraph up through the first embodiment in this paragraph wherein the mercaptan rich stream has a T5 boiling point of about 20° C. to about 40° C., a T95 boiling point of about 95° C. to about 105° C., and a final boiling point of about 110° C. to about 130° C., and the second mercaptan lean stream has a T5 boiling point of about 100° C. to about 110° C., a T95 boiling point of about 210° C. to about 240° C., and a final boiling point of about 250° C. to about 280° C. An embodiment of the invention is one, any or all of prior embodiments in this paragraph up through the first embodiment in this paragraph wherein the second mercaptan lean stream has a T5 boiling point of about 20° C. to about 40° C., a T95 boiling point of about 55° C. to about 65, and a final boiling point of about 70° C. to about 75° C., and the mercaptan rich stream has a T5 boiling point of about 60° C. to about 70° C., a T95 boiling point of about 210° C. to about 240° C., and a final boiling point of about 250° C. to about 280° C. An embodiment of the invention is one, any or all of prior embodiments in this paragraph up through the first embodiment in this paragraph wherein the mercaptan rich stream has a T5 boiling point of about 20° C. to about 40° C., a T95 boiling point of about 210° C. to about 240° C., and a final boiling point of about 250° C. to about 280° C. An embodiment of the invention is one, any or all of prior embodiments in this paragraph up through the first embodiment in this paragraph wherein separating the at least the portion of the low sulfur stream into at least two streams comprises separating the at least the portion of the low sulfur stream into the mercaptan rich stream, the overhead stream, and a thiophene rich stream. An embodiment of the invention is one, any or all of prior embodiments in this paragraph up through the first embodiment in this paragraph wherein the mercaptan rich stream has a T5 boiling point of about 20° C. to about 40° C., a T95 boiling point of about 95° C. to about 105° C., and a final boiling point of about 110° C. to about 130° C., and the thiophene rich stream has a T5 boiling point of about 100° C. to about 110° C., a T95 boiling point of about 210° C. to about 240° C., and a final boiling point of about 250° C. to about 280° C. An embodiment of the invention is one, any or all of prior embodiments in this paragraph up through the first embodiment in this paragraph wherein the adsorbent zone contains an adsorbent comprising at least one of a molecular sieve, metal loaded alumina, reactive metal adsorbent, and an alumina-zeolite composite adsorbent. An embodiment of the invention is one, any or all of prior embodiments in this paragraph up through the first embodiment in this paragraph wherein the adsorbent zone comprises at least two adsorbent beds. An embodiment of the invention is one, any or all of prior embodiments in this paragraph up through the first embodiment in this paragraph wherein the mercaptan rich stream alternately flows to the at least two adsorbent beds. An embodiment of the invention is one, any or all of prior embodiments in this paragraph up through the first embodiment in this paragraph wherein the adsorbent zone is operated at a temperature of about 15° C. to about 35° C. An embodiment of the invention is one, any or all of prior embodiments in this paragraph up through the first embodiment in this paragraph further comprising pre-treating the at least the portion of the naphtha feed stream. An embodiment of the invention is one, any or all of prior embodiments in this paragraph up through the first embodiment in this paragraph wherein pre-treating the at least the portion of the naphtha feed stream comprises treating the naphtha feed in a caustic extraction zone to form a reduced sulfur stream; separating the reduced sulfur stream into an overhead stream having a T5 boiling point of about 0° C. to about 10° C., a T95 boiling point of about 55° C. to about 65° C., and a final boiling point of about 65° C. to about 70° C., and a bottoms stream having a T5 boiling point of about 60° C. to about 70° C., a T95 boiling point of about 210° C. to about 240° C., and a final boiling point of about 250° C. to about 280° C., and wherein the bottoms stream comprises the at least the portion of the naphtha feed stream. An embodiment of the invention is one, any or all of prior embodiments in this paragraph up through the first embodiment in this paragraph wherein pre-treating the at least the portion of the naphtha feed stream comprises treating the naphtha feed stream in a selective hydrogenation reaction zone under selective hydrogenation conditions in the presence of a selective hydrogenation catalyst to form a hydrogenated naphtha feed stream; and wherein introducing the at least the portion of the naphtha feed stream to the selective hydrodesulfurization zone comprises introducing at least a portion of the hydrogenated naphtha feed stream to the selective hydrodesulfurization zone. An embodiment of the invention is one, any or all of prior embodiments in this paragraph up through the first embodiment in this paragraph further comprising separating the low sulfur stream into a gas stream and a liquid low sulfur stream; and wherein separating the at least the portion of the low sulfur stream into the at least two streams comprises separating the liquid low sulfur stream into the at least two streams.

A second embodiment of the invention is a process for reducing the sulfur content of full range naphtha comprising: introducing at least a portion of a naphtha feed stream to a selective hydrodesulfurization zone under selective hydrodesulfurization conditions in the presence of a selective hydrodesulfurization catalyst to form a low sulfur stream, the low sulfur stream containing mercaptan compounds and thiophene compounds; separating at least a portion of the low sulfur stream into at least three streams, a mercaptan rich stream containing mercaptan compounds and thiophene compounds, an overhead stream containing hydrogen sulfide and liquid petroleum gas; and a second mercaptan lean stream; treating the mercaptan rich stream in an adsorbent zone to remove at least a portion of the mercaptan compounds and the thiophene compounds to form a first mercaptan lean stream. A third embodiment of the invention is an apparatus for reducing the sulfur content of naphtha comprising a selective hydrodesulfurization zone having an inlet and an outlet; a stripper column having an inlet, an overhead vapor outlet, and a liquid outlet, the outlet of the selective hydrodesulfurization zone being in fluid communication with the inlet of the stripper column; and an adsorbent zone having an inlet and an outlet, the liquid outlet of the stripper column being in fluid communication with the inlet of the adsorbent zone. An embodiment of the invention is one, any or all of prior embodiments in this paragraph up through the third embodiment in this paragraph wherein the stripper column has a second liquid outlet, and further comprising a second adsorbent zone having an inlet and an outlet, the second liquid outlet of the stripper column being in fluid communication with the inlet of the second adsorbent zone. An embodiment of the invention is one, any or all of prior embodiments in this paragraph up through the third embodiment in this paragraph further comprising a caustic extraction zone having an inlet and an outlet; a splitter column having an inlet, an overhead outlet, and a liquid outlet, the outlet of the caustic extraction zone being in fluid communication with the inlet of the splitter column, and the liquid outlet of the splitter column being in fluid communication with the inlet of the selective hydrodesulfurization zone. An embodiment of the invention is one, any or all of prior embodiments in this paragraph up through the third embodiment in this paragraph further comprising a selective hydrogenation reaction zone having an inlet and an outlet, the outlet of the selective hydrogenation reaction zone being in fluid communication with the inlet of the selective hydrodesulfurization zone. An embodiment of the invention is one, any or all of prior embodiments in this paragraph up through the third embodiment in this paragraph further comprising a separator having an inlet, and vapor outlet, and a liquid outlet, the inlet of the separator being in fluid communication with the outlet of the selective hydrodesulfurization zone, the liquid outlet of the separator being in fluid communication with the inlet of the stripper column.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for reducing the sulfur content of full range naphtha comprising:
   introducing at least a portion of a naphtha feed stream to a selective hydrodesulfurization zone under selective hydrodesulfurization conditions in the presence of a selective hydrodesulfurization catalyst to form a low sulfur stream, the low sulfur stream containing mercaptan compounds and thiophene compounds;
   separating at least a portion of the low sulfur stream into at least two streams, a mercaptan rich stream containing mercaptan compounds and thiophene compounds, and an overhead stream containing hydrogen sulfide and liquid petroleum gas, and a thiophene rich stream; and
   treating the mercaptan rich stream in an adsorbent zone to remove at least a portion of the mercaptan compounds and the thiophene compounds to form a mercaptan lean stream.

2. The process of claim 1 wherein the mercaptan rich stream has a T5 boiling point of about 20° C. to about 40° C., a T95 boiling point of about 95° C. to about 105° C., and a final boiling point of about 110° C. to about 130° C., and the second mercaptan lean stream has a T5 boiling point of about 100° C. to about 110° C., a T95 boiling point of about 210° C. to about 240° C., and a final boiling point of about 250° C. to about 280° C.

3. The process of claim 1 wherein the second mercaptan lean stream has a T5 boiling point of about 20° C. to about 40° C., a T95 boiling point of about 55° C. to about 65° C., and a final boiling point of about 70° C. to about 75° C., and the mercaptan rich stream has a T5 boiling point of about 60° C. to about 70° C., a T95 boiling point of about 210° C. to about 240° C., and a final boiling point of about 250° C. to about 280° C.

4. The process of claim 1 wherein the mercaptan rich stream has a T5 boiling point of about 20° C. to about 40° C., a T95 boiling point of about 210° C. to about 240° C., and a final boiling point of about 250° C. to about 280° C.

5. The process of claim 1, wherein the mercaptan rich stream has a T5 boiling point of about 20° C. to about 40° C., a T95 boiling point of about 95° C. to about 105° C., and a final boiling point of about 110° C. to about 130° C., and the thiophene rich stream has a T5 boiling point of about 100° C. to about 110° C., a T95 boiling point of about 210° C. to about 240° C., and a final boiling point of about 250° C. to about 280° C.

6. The process of claim 1 wherein the adsorbent zone contains an adsorbent comprising at least one of a molecular sieve, metal loaded alumina, reactive metal adsorbent, and an alumina-zeolite composite adsorbent.

7. The process of claim 1 wherein the adsorbent zone comprises at least two adsorbent beds.

8. The process of claim 1 wherein the mercaptan rich stream alternately flows to the at least two adsorbent beds.

9. The process of claim 1 further comprising:
   treating the naphtha feed stream in a caustic extraction zone to form a reduced sulfur stream;
   separating the reduced sulfur stream into an overhead stream having a T5 boiling point of about 0° C. to about 10° C., a T95 boiling point of about 55° C. to about 65° C., and a final boiling point of about 65° C. to about 70° C., and a bottoms stream having a T5 boiling point of about 60° C. to about 70° C., a T95 boiling point of about 210° C. to about 240° C., and a final boiling point of about 250° C. to about 280° C., and wherein the bottoms stream comprises the at least the portion of the naphtha feed stream being introduced to the selective hydrodesulfurization zone.

10. The process of claim 1 further comprising:
   treating the naphtha feed stream in a selective hydrogenation reaction zone under selective hydrogenation conditions in the presence of a selective hydrogenation catalyst to form a hydrogenated naphtha feed stream; and
   wherein introducing the at least the portion of the naphtha feed stream to the selective hydrodesulfurization zone comprises introducing at least a portion of the hydrogenated naphtha feed stream to the selective hydrodesulfurization zone.

11. The process of claim 10 further comprising:
   separating the low sulfur stream into a gas stream and a liquid low sulfur stream; and
   wherein separating the at least the portion of the low sulfur stream into the at least two streams comprises separating the liquid low sulfur stream into the at least two streams.

12. A process for reducing the sulfur content of full range naphtha comprising:
   introducing at least a portion of a naphtha feed stream to a selective hydrodesulfurization zone under selective hydrodesulfurization conditions in the presence of a selective hydrodesulfurization catalyst to form a low sulfur stream, the low sulfur stream containing mercaptan compounds and thiophene compounds;
   separating at least a portion of the low sulfur stream into at least three streams, a mercaptan rich stream containing mercaptan compounds and thiophene compounds, an overhead stream containing hydrogen sulfide and liquid petroleum gas; and a second mercaptan lean stream;

treating the mercaptan rich stream in an adsorbent zone to remove at least a portion of the mercaptan compounds and the thiophene compounds to form a first mercaptan lean stream.

13. An apparatus for reducing the sulfur content of naphtha comprising:
a selective hydrodesulfurization zone having an inlet and an outlet;
a stripper column having an inlet, an overhead vapor outlet, and a liquid outlet, the outlet of the selective hydrodesulfurization zone being in fluid communication with the inlet of the stripper column;
an adsorbent zone having an inlet and an outlet, the liquid outlet of the stripper column being in fluid communication with the inlet of the adsorbent zone;
a caustic extraction zone having an inlet and an outlet; and
a splitter column having an inlet, an overhead outlet, and a liquid outlet, the outlet of the caustic extraction zone being in fluid communication with the inlet of the splitter column, and the liquid outlet of the splitter column being in fluid communication with the inlet of the selective hydrodesulfurization zone.

14. The apparatus of claim 13 wherein the stripper column has a second liquid outlet, and further comprising:
a second adsorbent zone having an inlet and an outlet, the second liquid outlet of the stripper column being in fluid communication with the inlet of the second adsorbent zone.

15. The apparatus of claim 13 further comprising:
a selective hydrogenation reaction zone having an inlet and an outlet, the outlet of the selective hydrogenation reaction zone being in fluid communication with the inlet of the selective hydrodesulfurization zone.

16. The apparatus of claim 15 further comprising:
a separator having an inlet, and vapor outlet, and a liquid outlet, the inlet of the separator being in fluid communication with the outlet of the selective hydrodesulfurization zone, the liquid outlet of the separator being in fluid communication with the inlet of the stripper column.

17. The process of claim 12 wherein the mercaptan rich stream has a T5 boiling point of about 20° C. to about 40° C., a T95 boiling point of about 95° C. to about 105° C., and a final boiling point of about 110° C. to about 130° C., and the second mercaptan lean stream has a T5 boiling point of about 100° C. to about 110° C., a T95 boiling point of about 210° C. to about 240° C., and a final boiling point of about 250° C. to about 280° C.

18. The process of claim 12 wherein the second mercaptan lean stream has a T5 boiling point of about 20° C. to about 40° C., a T95 boiling point of about 55° C. to about 65° C., and a final boiling point of about 70° C. to about 75° C., and the mercaptan rich stream has a T5 boiling point of about 60° C. to about 70° C., a T95 boiling point of about 210° C. to about 240° C., and a final boiling point of about 250° C. to about 280° C.

* * * * *